United States Patent [19]

Yamaguchi et al.

[11] Patent Number: 4,724,268

[45] Date of Patent: Feb. 9, 1988

[54] PURIFICATION PROCESS OF 3,3'-DINITRODIPHENYL COMPOUNDS

[75] Inventors: Keizaburo Yamaguchi, Kawasaki; Kenichi Sugimoto, Yokohama; Yoshimitsu Tanabe, Yokohama; Teruyuki Nagata, Omuta; Akihiro Yamaguchi, Kamakura, all of Japan

[73] Assignee: Mitsui Toatsu Chemicals, Incorporated, Tokyo, Japan

[21] Appl. No.: 882,246

[22] Filed: Jul. 7, 1986

[30] Foreign Application Priority Data

Jul. 16, 1985 [JP] Japan ................................ 60-155166
Aug. 6, 1985 [JP] Japan ................................ 60-171785

[51] Int. Cl.⁴ ...................... C07C 147/06; C07C 79/36

[52] U.S. Cl. ........................................ 568/30; 568/33; 568/306; 568/333

[58] Field of Search ..................... 568/30, 33, 306, 333

[56] References Cited

U.S. PATENT DOCUMENTS

| | | | |
|---|---|---|---|
| 1,665,005 | 4/1928 | Foster | 568/932 |
| 2,392,137 | 1/1946 | Weiland et al. | 568/33 |
| 3,931,347 | 1/1976 | Rosenblatt et al. | 568/934 |
| 4,352,942 | 10/1982 | Onopchenko et al. | 568/306 |
| 4,361,704 | 11/1982 | Onopchenko et al. | 568/306 |
| 4,503,276 | 3/1985 | Nickson | 568/30 |
| 4,560,800 | 12/1985 | Bakshi et al. | 568/306 |

FOREIGN PATENT DOCUMENTS

| | | |
|---|---|---|
| 2530067 | 2/1977 | Fed. Rep. of Germany . |
| 1318860 | 5/1973 | United Kingdom . |

OTHER PUBLICATIONS

J. Lacroix, Chem. Abstracts 19:980 (1925).
B. Ciocca et al., Chem. Abstracts 40:7153 (1946).
G. Nazvanova et al., Chem. Abstracts 73:34962n (1970).
C. Buehler et al., J. Org. Chem., 4, 262 (1939).
A. Onopchenko et al., J. Org. Chem., 46, 5014 (1981).
Journal of Chemical Society, 125 767 (1924), E. Barnett et al.

*Primary Examiner*—Mary E. Ceperley
*Attorney, Agent, or Firm*—Fisher, Christen & Sabol

[57] ABSTRACT

A crude 3,3'-dinitrodiphenyl compound selected from 3,3'-dinitrodiphenylsulfone or 3,3'-dinitrobenzophenone is purified by reacting the crude 3,3'-dinitrodiphenyl compound with a lower alcohol in the presence of a base so as to convert practically the isomer or isomers, which contain one or more nitro groups at the ortho- or/and para-positions, only into the corresponding alkoxy compound or compounds thereof and then separating the alkoxy compound or compounds.

6 Claims, No Drawings

PURIFICATION PROCESS OF 3,3'-DINITRODIPHENYL COMPOUNDS

BACKGROUND OF THE INVENTION (a) Field of the Invention

This invention relates to a process for the purification of 3,3'-dinitrodiphenyl compounds such as 3,3'-dinitrodiphenylsulfone (hereinafter abbreviated as "3,3'-DNDS") and 3,3'-dinitrobenzophenone (hereinafter abbreviated as "3,3'-DNBP").

(b) Description of the Prior Art 3,3'-DNDS and 3,3'-DNBP are converted respectively into their corresponding 3,3'-diamino compounds, namely, 3,3'-diaminodiphenylsulfone and 3,3'-diaminobenzophenone, which are useful as heat-resistant high molecular monomers as well as intermediates for agricultural chemicals, medicines and dyes. These compounds are important especially as raw materials for heat-resistant polyamides, polyamide-imides and polyimides and as hardeners for epoxy resins.

It has conventionally been known to prepare 3,3'-DNDS by nitrating diphenyl sulfone with a mixed acid [J. Org. Chem., 4 262 (1939); Chem. Abs., 19 980 (1925)] or by subjecting diphenyl sulfide to simultaneous oxidation and nitration with fuming nitric acid [Chem. Abs., 40 7153 (1946)]. It has also been proposed to isolate 3,3'-DNDS as a byproduct upon nitration of benzene in the presence of sulfuric anhydride [Chem. Abs., 73 34962n (1970)]. It has also been known to isolate 3,3'-DNDS as a byproduct upon preparation of m-nitrobenzenesulfonic acid through sulfonation of nitrobenzene [Chem. Abs., 73 34962n (1970)].

It is however necessary to conduct recrystallization repeatedly by using a great deal of solvent for the isolation of 3,3'-DNDS in its purified form in the preparation process of 3,3'-DNDS from diphenyl sulfone or diphenyl sulfide, because the reaction product obtained by the nitration is a mixture of isomers which have been substituted by nitro groups at different positions. The yield is therefore lowered and substantial cost and labor are required for the recovery of the solvent used in the purification, the treatment and disposal of residual matter, etc., resulting in an increase to its price. As mentioned above, 3,3'-DNDS is also obtained as a by-product upon nitration of benzene in sulfuric anhydride or sulfonation of nitrobenzene. This approach is however accompanied by such drawbacks that its yield is low and since it is not prepared as the principal reaction product, its supply is not satisfactory and cannot meet the increased demand for same.

On the other hand, 3,3'-DNBP can be prepared by the nitration of benzophenone. In this process, the reaction product is a mixture containing isomers. In order to isolate the intended product, namely, the 3,3'-dinitro isomers only, it is indispensable to conduct its purification, i.e., recrystallization repeatedly by using a great deal of solvent [Journal of Chemical Society, 125 767 (1924)]. For this reason, the yield of 3,3'-DNBP is lowered to a significant extent and moreover, cumbersome steps and additional expenses are also required for the recovery of the solvent employed in the purification, the treatment and disposal of residual matter, etc.

It has recently been proposed to conduct the nitration of benzophenone in a large volume of fuming sulfuric acid so as to improve the selectivity for the meta-position [Journal of Organic Chemistry, 46 5014 (1981)]. As drawbacks of this process, may be mentioned that it requires fuming sulfuric acid, the concentration of which must be controlled within a narrow range, in a large volume and moreover, stringent control of reaction temperature and time is essential. In addition, the above process is accompanied by potential danger because the temperature has to be raised to 70° C. in spite of the use of fuming sulfuric acid of a relatively high concentration. Even when the process is carried out under such conditions, the purity of the resultant 3,3'-dinitro isomer is as low as 93.5%–93.7%.

Describing the above-proposed process further in detail, its characteristic feature resides in that benzophenone is dinitrated with a mixed acid, which contains fuming sulfuric acid at a high concentration in order to increase the selectivity for the 3,3'-dinitro isomer, and the reaction mixture is then heated to sulfonate the 2,3'-dinitro isomer and the like, byproducts of the nitration reaction, in a short period of time so as to facilitate their removal in subsequent treatment and disposal steps. The content of the 3,3'-dinitro isomer is 81–82% upon completion of the nitration. Since the reaction mixture is thereafter subjected to a heat treatment, mononitro derivatives, 2,3-dinitro isomer and the like are eliminated and depending on the conditions of the heat treatment, the amount of the 3,3'-dinitro isomer is also reduced. As a result, the yield of the 3,3'-dinitro isomer drops to 60–84%.

As has been described above, it is necessary to solve problems on the materials of apparatus for the above-described processes and to make a great deal of waste acids of high concentrations pollution-free. Moreover, the reaction products are mixtures of isomers and their purification is hence indispensable. Accordingly, the above-described processes are accompanied by various difficulties for their practice on industrial scales.

SUMMARY OF THE INVENTION

An object of this invention is to provide a process for providing useful 3,3'-dinitrodiphenyl compounds at economical prices and stably.

Another object of this invention is to provide a process for obtaining high-purity 3,3'-dinitrodiphenyl compounds with good yields from crude 3,3'-dinitrodiphenyl compounds, which have been obtained in accordance with various nitration processes and contain isomers, by a simple treatment.

The present inventors have carried out an extensive investigation with a view toward attaining the above objects. As a result, it has been found that when a crude 3,3'-dinitrodiphenyl compound containing one or more isomeric compounds is treated with a lower alcohol and a base, the isomeric compound or compounds substituted by nitro group or groups at the ortho- or/and para-positions are solely converted into the corresponding alkoxy compound or compounds without any substantial loss of the 3,3'-dinitrodiphenyl compound. It has also been found that since the solubility of the 3,3'-dinitrodiphenyl compound in the lower alcohol is low, the 3,3'-dinitrodiphenyl compound can be isolated in a highly-purified form with good yield through its separation from the dissolved alkoxy compound or compounds by simple filtration. The present invention has been completed on the basis of the above findings.

In one aspect of this invention, there is thus provided a process for the purification of a crude 3,3'-dinitrodiphenyl compound represented by the following general formula:

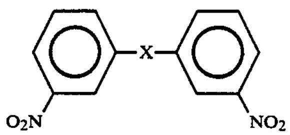

wherein X means an $-SO_2-$ or $-CO-$ group, said crude 3,3'-dinitrodiphenyl compound containing one or more isomeric compounds, which comprises treating the crude 3,3'-dinitrodiphenyl compound with a lower alcohol and a base so as to convert practically the isomer or isomers, which contain one or more nitro groups at the ortho- or/and para-positions, only into the corresponding alkoxy compound or compounds thereof and then separating the alkoxy compound or compounds.

When crude dinitrodiphenylsulfone is subjected, as an exemplary crude dinitrodiphenyl compound, to an alkoxylation reaction under relatively mild conditions in the presence of a lower alcohol and a base in accordance with the present invention, all isomeric compounds other than 3,3'-DNDS, in other words, 2,2'-dinitrodipheylsulfone, 2,3'-dinitrodiphenylsulfone, 3,4'-dinitrodiphenylsulfone, 4,4'-dinitrodiphenylsulfone and the like in each of which nitro groups are substituted at the ortho- and para-positions relative to the sulfonyl group of diphenylsulfone are reacted readily into their corresponding alkoxy compounds as a result of substitution of the nitro group or groups at the ortho- or/and para-positions but 3,3'-DNDS does not react at all since the nitro groups at the metaposition not active. Accordingly, 3,3'-DNDS can be purified without any substantial loss.

Furthermore, the solubility of this 3,3'-DNDS is low in the lower alcohol employed in the above process while the other reaction products, i.e., the alkoxy compounds have relatively higher solubility in the lower alcohol. As a result, 3,3'-DNDS can be obtained in a highly-purified form without any substantial loss through collection of deposited crystals by simple filtration after the reaction. Since 3,3'-DNDS remains in the deposited state during the alkoxylation reaction, it is also mentioned as a further merit that 3,3'-DNDS, obtained after its isolation, is free of such problems as mixing of impurities or coloration.

According to the above-described process of this invention, useful 3,3'-DNBP can be obtained with good yield from crude dinitrobenzophenone provided by the nitration of benzophenone or the like. Although the object, i.e., the purification has heretofore been achieved with low yield by repeating recrystallization, the process of this invention can achieve it by the extremely simple method, i.e., by treating the reaction mixture with the lower alcohol and base and moreover, 3,3'-DNBP contained in the crude product can be recovered without any substantial loss. Further, the materials employed in the process of this invention are all inexpensive and their recovery is easy. Therefore, the process of this invention is not only economical but also excellent as a pollution-free process.

DETAILED DESCRIPTION OF THE INVENTION

The process of this invention is effective in obtaining, with a high purity, a dinitrodiphenyl compound of the following formula:

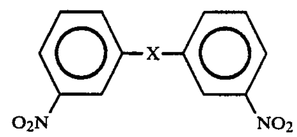

wherein X means an $-SO_2-$ or $-CO-$ group.

The starting crude dinitrodiphenyl compound to which the process of this invention is applied, for example, crude dinitrodiphenylsulfone is 3,3'-dinitrodiphenylsulfone containing the diphenylsulfone nitrated at the ortho- or p-position relative to the above-mentioned $-SO_2$ group. Most typically, may be mentioned that prepared by the nitration of diphenylsulfone or that produced by the nitration of 3-nitrodiphenylsulfone which has in turn been obtained by the Friedel-Crafts reaction of 3-nitrobenzenesulfonyl chloride and benzene. Dinitrodiphenylsulfone obtained by these processes may generally contain 3,3'-DNDS at a content of 60–95% or so and besides, isomeric compounds such as 2,2'-dinitrodiphenylsulfone, 2,3'-dinitrodiphenylsulfone and 3,4'-dinitrodiphenylsulfone at a total content of 5–40% or so, although their contents vary depending on the conditions for the nitration reaction.

On the other hand, the starting crude dinitrobenzophenone is usually prepared, most typically, by the nitration of benzophenone. As an alternative, it can also be prepared by nitrating 3-nitrobenzophenone which is in turn obtained by the Friedel-Crafts reaction of 3-nitrobenzoyl chloride and benzene. Dinitrobenzophenone obtained by these processes may generally contain 3,3'-DNBP at a content of 60–95% or so and besides, isomers such as 2,2'-dinitrobenzophenone, 2,3'-dinitrobenzophenone, 3,4'-dinitrobenzophenone and 4,4'-dinitrobenzophenone at a total content of 5–40% or so, although their contents vary depending on the conditions for the nitration reaction.

Most of these dinitro isomeric compounds may however be readily separated and removed by applying the process of this invention.

As exemplary lower alcohols useful in the practice of the process of this invention, may be mentioned lower aliphatic monohydric alcohols such as methanol, ethanol and propanol, alicyclic alcohols such as cyclohexanol, aromatic alcohol such as benzyl alcohol, lower polyhydric alcohols such as ethylene glycol, etc. With the reaction velocity of alkoxylation and the expenses for recovery and the like in view, lower aliphatic monohydric alcohols are preferred with aliphatic monohydric alcohols having 5 or less carbon atoms being more preferred.

No particular limitation is imposed on the amount of an alcohol to be used, so long as it is at least equal in moles to the total content of isomers other than the 3,3'-dinitrodiphenyl compound contained in the crude dinitrodiphenyl compound. Serving as a solvent too, it is usually employed in such an amount that the resulting reaction system can be stirred. Namely, it is sufficient to use the alcohol in an amount 1–5 times by weight the starting crude dinitrodiphenyl compound. Another solvent inert to the starting material and alcohol may also be added to conduct the reaction, especially, in order to use the alcohol in a small amount not exceeding 1 times by volume the starting material. As such additional solvents, may be mentioned aromatic hydrocarbons such as benzene, toluene and monochlorobenzene, halogenated hydrocarbons such as 1,2-dichloroethane and 1,1,2-trichloroethane, ethers such as dioxane, diglyme and tetrahydrofuran, ketones such as acetone and methyl ethyl ketone, aprotic polar solvents such as N,N-dimethylformamide, N-methylpyrrolidone, 1,3-dimethyl-2-imidazolidinone and sulfolane, and water.

As exemplary bases useful in the practice of the process of this invention, may be mentioned the hydroxides, carbonates, bicarbonates, sulfites and bisulfites of alkali metals and alkaline earth metals, such as potassium carbonate, sodium carbonate, potassium hydroxide, sodium hydroxide and calcium hydroxide. Among these bases, the hydroxide or carbonate of sodium or potassium is preferred. The particularly-preferred base is sodium hydroxide for its low price. Besides, no inconvenience is encountered even if a compound prepared in advance as an alcoholate such as sodium methoxide, sodium ethoxide or potassium butoxide is employed. The base may be used in any amounts so long as its content is stoichiometrically equivalent to the total contents of isomers other than 3,3'-dinitro isomer contained in the starting crude dinitrodiphenyl compound. Preferably, 1.5–5 equivalents are sufficient.

The reaction temperature is chosen in such a way that a suitable reaction velocity is achieved in the reaction system. Usually, the reaction is carried out at the boiling point of the alcohol employed. In order to accelerate the reaction, the reaction may be carried out under elevated pressure at a temperature above the boiling point of the alcohol employed.

The progress of the reaction can be observed by thin-layer chromatography or high performance liquid chromatography. In the process of this invention, it is possible to add, as a catalyst for accelerating the reaction, a phase transfer catalyst such as quaternary ammonium salt, quaternary phosphonium salt, large cyclic polyether such as crown ether, nitrogen-containing large cyclic polyether such as cryptate, nitrogen-containing linear polyether, or polyethylene glycol or an alkyl ether thereof.

The process of the present invention may generally be practised in the following manner. A starting material, prescribed amounts of a base and alcohol, and when added, another solvent are charged in a reactor and are reacted at the temperature of the boiling point of the alcohol employed or at a temperature lower than the boiling point. After completion of the reaction, the reaction mixture is cooled and the deposited 3,3'-dinitrodiphenyl compound is collected by filtration to obtain the 3,3'-dinirodiphenyl compound in a high-purity form.

The present invention will hereinafter be described in further detail by the following Examples.

EXAMPLE 1

In a reactor fitted with a thermometer and stirrer, 440 g of industrial 98% sulfuric acid and 113.5 g (0.5 mole) of 3-nitrobenzophenone were charged. While dissolving 3-nitrobenzophenone under stirring, the reaction mixture was cooled and its temperature was maintained within the range of 0°–2° C. At the same temperature, 36 g of fuming nitric acid having a specific gravity of 1.52 was added dropwise over 2 hours. After completion of the dropwise addition, the cooling bath was removed and the temperature of the reaction mixture was allowed to rise to room temperature, where it was aged for 5 hours.

After completion of the reaction, the reaction mixture was poured in 1.5 l of ice water and the resultant crystals were collected by filtration. After washing the crystals with water, they were dried. They were crude 3,3'-DNBP. The yield was 132.5 g (97.4%) and its analysis by high performance liquid chromatography (HPLC) gave the following results.

| Results of HPLC Analysis | |
|---|---|
| 2,2'-DNBP | trace |
| 2,3'-DNBP | 16.8% |
| 3,3'-DNBP | 75.1% |
| 3,4'-DNBP | 7.8% |

Charged in a reactor equipped with a thermometer, stirrer and reflux condenser were 27.9 (0.1 mole) of the above crude dinitrobenzophenone, 2.8 g (0.09 mole) of sodium methylate and 85 ml of isobutanol. They were reacted for 8 hours under reflux of isobutanol. After cooling the reaction mixture, the deposited crystals were collected by filtration, washed and then dried to obtain 20.9 g of 3,3'-DNBP (yield: 74.9%). Its melting point was 143–147° C. and its purity was analyzed by high performance liquid chromatography.

| Results of HPLC Analysis | |
|---|---|
| 2,2'-DNBP | 0 |
| 2,3'-DNBP | 0.51% |
| 3,3'-DNBP | 97.1% |
| 3,4'-DNBP | 0.48% |
| Others | 1.9% |

EXAMPLE 2

In a reactor, 191 g of 22.5% fuming sulfuric acid was charged. While maintaining the fuming sulfuric acid at temperatures below 20° C., 20 g of benzophenone was added and dissolved. Thereafter, while maintaining the temperature at 15°–20° C., a mixed acid which had been prepared on the side from 16.5 g of 90% nitric acid and 57.3 g of 22.5% fuming sulfuric acid was added dropwise over 2 hours. After the dropwise addition, the reaction mixture was aged at the same temperature for 0.5 hour and was then heated to 70° C., where it was maintained for 1 hour. After cooling, the reaction mixture was poured in 200 g of ice water and the resultant deposit was collected by filtration, washed with water and then dried. It was crude 3,3'-DNBP. Results of its analysis by high performance liquid chromatography were as given below. Its yield was 22.7 g (76%).

| Results of HPLC Analysis | |
|---|---|
| 2,3'-DNBP | 0 |
| 3,3'-DNBP | 93% |
| 3,4'-DNBP | 5.6% |
| Others | 1.4% |

The above crude 3,3'-DNBP was reacted with 1.4 g of potassium carbonate, 75 ml of ethanol and 25 ml of water under reflux for 5 hours. After cooling, the resultant crystals were collected by filtration, washed and then dried to obtain 20.9 g of 3,3'-DNBP (yield: 92%). Its analysis by high performance liquid chromatography gave the following results.

| Results of HPLC Analysis | |
|---|---|
| 3,3'-DNBP | 99.2% |
| 3,4'-DNBP | 0.41% |
| Others | 0.39% |

EXAMPLE 3

A reactor was charged with 440 g of 25% fuming sulfuric acid. The reactor was cooled to maintain the fuming sulfuric acid at 0°-2° C. At the same temperature, 113.5 g of benzophenone was charged, followed by a dropwise addition of 70.7 g of fuming nitric acid having a specific gravity of 1.52 over 3 hours.

After completion of the dropwise addition, the cooling bath was removed and the internal temperature was raised to 25° C., where the reaction mixture was stirred for 3 hours. The reaction mixture was then poured in 1.5 l of ice water and the resultant deposit was collected by filtration, washed with water and dried to obtain 132.7 g of crude 3,3'-DNBP (yield: 97.5%). Its analysis by high performance liquid chromatography gave the following results.

| Results of HPLC Analysis | |
|---|---|
| 2,3'-DNBP | 13.9% |
| 3,3'-DNBP | 79.7% |
| 3,4'-DNBP | 6.2% |
| Others | 0.2% |

Thereafter, 27.2 g of the above crude 3,3'-DNBP, 1.36 g of potassium hydroxide and 100 ml of methanol were charged in a pressure reactor and reacted for 5 hours at 110° C. and 3.8 kg/cm$^2$. After cooling, the resultant crystals were collected by filtration, washed and the dried to obtain 21.5 g of 3,3'-DNBP (yield: 79%). Its analysis by high performance liquid chromatography gave the following results.

| Results of HPLC Analysis | |
|---|---|
| 2,3'-DNBP | 0.2% |
| 3,3'-DNBP | 98.6% |
| 3,4'-DNBP | 0.8% |
| Others | 0.4% |

EXAMPLE 4

Reacted for 5 hours at 110°-115° C. were 27.2 g of the crude dinitrobenzophenone obtained in Example 3, 0.8 g of caustic soda, 5 ml of methanol and 50 ml of diethylene glycol dimethyl ether (diglyme).

The reaction mixture was analyzed by high performance liquid chromatography. The following results were obtained.

| Results of HPLC Analysis | |
|---|---|
| 2,2'-DNBP | 0 |
| 2,3'-DNBP | 0.81% |
| 3,3'-DNBP | 77.6% |
| 3,4'-DNBP | 1.33% |
| Unidentified component (a) | 14.8% |
| Unidentified component (b) | 3.25% |
| Unidentified component (c) | 2.2% |

The peak of the unidentified component (a) was confirmed to coincide with the peak of nitromethoxybenzophenone obtained by the Friedel-Craft reaction of 3-nitrobenzoyl chloride and anisole.

EXAMPLE 5

A reaction was conducted by using 8.4 g of n-butoxy potassium and 85 ml of N,N-dimethylformamide per 27.2 g of the crude dinitrobenzophenone obtained in Example 3. After proceeding with the reaction for 7 hours at 120°-130° C., 100 ml of water was added to cool the reaction mixture. The deposited crystals were collected by filtration, washed and then dried, thereby obtaining 17.5 g of 3,3'-DNBP (yield: 64.3%).

Its purity was found to be 98.6% by high performance liquid chromatography.

EXAMPLE 6

In a reactor fitted with a thermometer and stirrer, 440 g of industrial 98% sulfuric acid and 109 g (0.5 mole) of diphenylsulfone were charged. While dissolving diphenylsulfone under stirring, the reaction mixture was cooled and its temperature was maintained within the range of 0°-2° C. At the same temperature, 70.7 g of fuming nitric acid having a specific gravity of 1.52 was added dropwise over 2 hours. After completion of the dropwise addition, the cooling bath was removed and the temperature of the reaction mixture was allowed to rise to room temperature, where it was aged for 5 hours. After completion of the reaction, the reaction mixture was poured in 1.5 l of ice water and the resultant crystals were collected by filtration. After washing the crystals with water, they were dried. They were crude 3,3'-DNDS. The yield was 151.5 g (98.3%) and its analysis by high performance liquid chromatography (HPLC) gave the following results.

| Results of HPLC Analysis | |
|---|---|
| 2,2'-DNDS | trace |
| 2,3'-DNDS | 9.59% |
| 3,3'-DNDS | 86.3% |
| 3,4'-DNDS | 4.22% |

Charged in a reactor equipped with a thermometer, stirrer and reflux condenser were 30.8 g (0.1 mole) of the above crude dinitrodiphenylsulfone, 1.2 g (0.03 mole) of caustic soda, 70 ml of methanol, 0.5 g of triethylbenzylammonium chloride and 30 ml of water. They were reacted for 8 hours under reflux of the methanol-water solution. After cooling the reaction mixture, the deposited crystals were collected by filtration, washed and then dried to obtain 26.8 g of 3,3'-DNDS (yield: 87.0% based on the crude DNDS). Its melting point was 197°-200° C. and its purity by high performance liquid chromatography was as follow:

| Results of HPLC Analysis | |
|---|---|
| 2,2'-DNDS | 0 |
| 2,3'-DNDS | 0.66% |
| 3,3'-DNDS | 98.23% |
| 3,4'-DNDS | 1.11% |

EXAMPLE 7

In a reactor fitted with a thermometer and stirrer, 131.6 g (0.5 moles) of 3-nitrodiphenylsulfone and 300 g of industrial 98% sulfuric acid were charged, followed by a dropwise addition at 0°-2° C. of 36 g of fuming nitric acid having a specific gravity of 1.52. The nitration reaction and post treatment were conducted in the same manner as in Example 6, thereby obtaining 152.1 g of crude dinitrodiphenylsulfone (yield: 98.7%). Its analysis by high performance liquid chromatography gave the following results.

| Results of HPLC Analysis | |
|---|---|
| 2,3'-DNDS | 3.54% |
| 3,3'-DNDS | 93.85% |
| 3,4'-DNDS | 2.61% |

The crude dinitrodiphenylsulfone (30.8 g; 0.1 mole) was reacted with 1.38 g (0.01 mole) of anhydrous potassium carbonate and 100 ml of ethanol under reflux for 5 hours.

After cooling, the resultant crystals were collected by filtration, washed and then dried to obtain 28.7 g of 3,3'-DNDS (yield: 93.2% based on the crude DNDS). Its melting point was 198°-201° C. and Its analysis by high performance liquid chromatography gave the following results.

| Results of HPLC Analysis | |
|---|---|
| 2,3'-DNDS | 0.43% |
| 3,3'-DNDS | 98.76% |
| 3,4'-DNDS | 0.81% |

EXAMPLE 8

The nitration reaction of Example 6 was carried out at nitration temperatures of 30°-40° C. by using nitric acid having a specific gravity of 1.38 instead of the fuming nitric acid the specific gravity of which was 1.52. As a result, crude dinitrodiphenylsulfone was obtained with a yield of 96.9%. Its composition was found to be as follows by high performance liquid chromatography.

| Results of HPLC Analysis | |
|---|---|
| 2,2'-DNDS | trace |
| 2,3'-DNDS | 17.16% |
| 3,3'-DNDS | 71.7% |
| 3,4'-DNDS | 11.09% |

The above crude dinitrodiphenylsulfone (30.8 g; 0.1 mole) were reacted with 2 g of caustic soda and 75 ml of butanol at 105°-110° C. for 7 hours.

After cooling, the resultant crystals were collected by filtration, washed and then dried to obtain 21 g of 3,3'-DNDS (yield: 68.8% based on the crude DNDS). Its purity by high performance liquid chromatography was as follow:

| Results of HPLC Analysis | |
|---|---|
| 2,2'-DNDS | 0 |
| 2,3'-DNDS | 2.29% |
| 3,3'-DNDS | 96.55% |
| 3,4'-DNDS | 1.16% |

EXAMPLE 9

A reaction was conducted under reflux for 15 hours by using 0.8 g of caustic soda, 10 ml of methanol and 75 ml of toluene per 30.8 g of the crude dinitrodiphenylsulfone obtained in Example 6. After cooling, the resultant crystals were collected by filtration, washed and then dried, thereby obtaining 26 g of 3,3'-DNDS (yield: 84.4% based on the crude DNDS). Its purity by high performance liquid chromatography was as follow:

| Results of HPLC Analysis | |
|---|---|
| 2,2'-DNDS | 0 |
| 2,3'-DNDS | 0.77% |
| 3,3'-DNDS | 98.34% |
| 3,4'-DNDS | 0.89% |

EXAMPLE 10

The crude dinitrodiphenylsulfone (15.4 g) obtained in Example 8 was reacted with 0.8 g of caustic soda, 5 ml of methanol and 50 ml of diethylene glycol dimethyl ether (diglyme) at 80°-85° C. for 5 hours. The reaction mixture was analyzed by high performance liquid chromatography. The following results were obtained.

| Results of HPLC Analysis | |
|---|---|
| 2,2'-DNDS | 0 |
| 2,3'-DNDS | 0.81% |
| 3,3'-DNDS | 67.16% |
| 3,4'-DNDS | 0.65% |
| Unidentified component (a) | 28.78% |
| Unidentified component (b) | 0.63% |
| Unidentified component (c) | 0.77% |
| Unidentified component (d) | 1.20% |

The peak of the unidentified component (a) was confirmed to coincide with the peak of nitromethoxydiphenylsulfone obtained by the Friedel-Craft reaction of 3-nitrobenzenesulfonyl chloride and anisole.

EXAMPLE 11

The alkoxylation reaction of Example 7 was carried out in the same manner except that n-pentanol was used in lieu of ethanol and the reaction was conducted at 105°-110° C. for 8 hours. As a result, 3,3'-DNDS having a purity of 97.23% as analyzed by high performance liquid chromatography was obtained (yield: 92.8% based on the crude DNDS).

What is claimed is:

1. Process for the purification of a crude 3,3'-dinitrodiphenyl compound represented by the following formula:

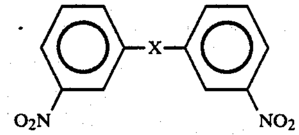

wherein X means an $-SO_2-$or$-CO-$ group, said crude 3,3'-dinitrodiphenyl compound containing one or more isomeric compounds, which comprises alkoxylating the crude 3,3'-dinitrodiphenyl compound with a lower alcohol and a base so as to convert only the isomer or isomers, which contain one or more nitro groups at the ortho-or/and para-positions, into the corresponding ortho or para alkoxy compound or compounds and then separating the alkoxy compound or compounds from the crude 3,3'-dinitrodiphenyl compound to provide the purified compounds.

2. The process as claimed in claim 1 wherein the 3,3'-dinitrodiphenyl compound compound is 3,3'-dinitrodiphenylsulfone.

3. The process as claimed in claim 1 wherein the 3,3-dinitrodiphenyl compound is 3,3'-dinitrobenzophenone.

4. The process as claimed in claim 1 wherein the base is the hydroxide, carbonate, bicarbonate, sulfite or bisulfite of an alkali metal or alkaline earth metal.

5. The process as claimed in claim 4 wherein the base is sodium hydroxide, potassium hydroxide, sodium carbonate or potassium carbonate.

6. The process as claimed in claim 1 wherein the base is an alcoholate which has been prepared in advance of the purification process.

* * * * *